(12) United States Patent
Harren et al.

(10) Patent No.: US 7,863,496 B2
(45) Date of Patent: Jan. 4, 2011

(54) SELF-CLOSING ANTISEPTIC PLASTER

(75) Inventors: Ernst-Diethelm Harren, Steinhausen (CH); Marc Ulrich Lehmann, Herrliberg (CH)

(73) Assignee: Vostra-Med AG, Cham (CH)

( * ) Notice: Subject to any disclaimer, the term of this patent is extended or adjusted under 35 U.S.C. 154(b) by 122 days.

(21) Appl. No.: 11/665,937

(22) PCT Filed: Oct. 18, 2005

(86) PCT No.: PCT/CH2005/000607
§ 371 (c)(1), (2), (4) Date: May 8, 2007

(87) PCT Pub. No.: WO2006/042429
PCT Pub. Date: Apr. 27, 2006

(65) Prior Publication Data
US 2008/0119775 A1    May 22, 2008

(30) Foreign Application Priority Data
Oct. 20, 2004   (CH) .................................... 1729/04

(51) Int. Cl.
*A61F 13/00* (2006.01)
*A61F 13/02* (2006.01)
*A61M 5/32* (2006.01)

(52) U.S. Cl. .............................. 602/42; 602/54; 602/58; 604/174; 604/180; 604/304; 604/307; 604/513

(58) Field of Classification Search ................. 602/42, 602/48, 54, 58, 52; 128/850; 604/304, 307, 604/513, 167.02, 288.02, 180; 424/443, 424/445, 448, 449; 606/153; 428/425.5, 428/428, 429, 446, 447
See application file for complete search history.

(56) References Cited

U.S. PATENT DOCUMENTS 3,367,332 A * 2/1968 Groves ....................... 604/290

(Continued)

FOREIGN PATENT DOCUMENTS

EP        0 368 264 A1    5/1990

(Continued)

OTHER PUBLICATIONS

International Search Report, Mar. 2006.

*Primary Examiner*—Patricia M Bianco
*Assistant Examiner*—Keri J Nicholson
(74) *Attorney, Agent, or Firm*—Collard & Roe, P.C.

(57) ABSTRACT

A self-closing antiseptic plaster (1) for puncturing blood vessels, muscle tissue, tissue, skin, organs (biopsy) or bone marrow is puncturable by cannulas, needles or the like. It has a backing layer (2), a sealing layer (5) made of a material having an elastic restoring force and a skin adhesive layer (3) applied to the underside U of the backing layer (2), the sealing layer being applied to the backing layer (2) by means of an adhesive layer (4). The backing layer (2) is usually thin. The backing layer (2), the sealing layer (5), the adhesive layer (4) and the skin adhesive layer (3) are transparent or approximately transparent in the entire area or at least in a superimposed partial area. The backing layer (2) and the sealing layer (5) are made of thin and soft materials so that any puncture site is visible and/or palpable through the self-closing antiseptic plaster (1). The advantages include the fact that the antiseptic state at the puncture site is preserved before, during and after the puncturing.

14 Claims, 1 Drawing Sheet

U.S. PATENT DOCUMENTS

| | | | |
|---|---|---|---|
| 5,015,228 A | 5/1991 | Columbus et al. | |
| 5,330,452 A | 7/1994 | Zook | |
| 5,486,158 A * | 1/1996 | Samuelsen | 602/46 |
| 5,728,071 A * | 3/1998 | Watson et al. | 604/180 |
| 6,245,959 B1 * | 6/2001 | Ohira et al. | 602/41 |
| 2002/0161332 A1 * | 10/2002 | Ramey | 604/164.07 |

FOREIGN PATENT DOCUMENTS

EP     0 424 165 A1     4/1991

* cited by examiner

SELF-CLOSING ANTISEPTIC PLASTER

CROSS REFERENCE TO RELATED APPLICATIONS

Applicants claim priority under 35 U.S.C. §119 of Swiss Application No, 1729/04 filed Oct. 20, 2004. Applicants also claim priority under 35 U.S.C. §365 of PCT/CH2005/000607 filed Oct. 18, 2005. The international application under PCT article 21(2) was not published in English.

The invention relates to a self-closing antiseptic. plaster according to patent claim 1. It is intended for use on a human or animal body.

The invention relates in particular to a self-closing antiseptic plaster for puncturing blood vessels, muscle tissue, tissue, skin, organs (biopsy) and bone marrow, which can be punctured by cannulas or needles or, the like and is transparent in at least a partial area.

In this area of medical applications, there is a demand for antiseptically sealing the area in immediate proximity to the puncture site before, during and after the puncture in the simplest possible and most reliable way and thus maintaining this state for a definable period of time.

This is accomplished in the traditional manner by first disinfecting the site to be punctured, e.g., with a disinfectant by a spray method or the like, then performing the puncture and the associated invasive, medical procedure using a sterile needle or cannula or the like and finally covering the puncture site with a suitable agent, e.g., a plaster or a dressing, for the purpose of hemostasis.

U.S. Pat. No. 5,015,228 describes a disinfectant plaster that is applied to the respective location on the patient's skin even before the puncture. This is thus a plaster that is puncturable and to this end is transparent in an area provided for this. This plaster has a backing layer which has a recess in a partial area. A transparent puncturable and self-resealing sealing layer with disinfectant properties is applied to the backing layer and over the recess. The bottom side of the backing layer is provided with a skin adhesive layer, i.e., an adhesive that is tolerated well by the skin. As the sealing layer, a gel impregnated with disinfectant substances is used with this plaster. The disinfectant substances may have antibacterial, antiviral or fungicidal properties or a combination of these properties.

The plaster according to U.S. Pat. No. 5,015,228 should make it possible to stop having to disinfect the site to be punctured separately in advance, namely by applying the plaster directly to the site in question. The blood vessel to be punctured is visible and palpable through the recess in the backing layer and through the sealing layer with gel medium. Therefore, the skin of the patient comes in contact with the skin adhesive layer and the disinfectant sealing layer when the plaster is applied. When a puncture is performed through the sealing layer, the needle is disinfected, and when the needle is removed, the sealing layer with the gel medium closes up again immediately thanks to its resealing properties. The plaster may remain on the puncture wound after the puncture and should thus maintain the sterile condition in the area of the puncture site before, during and after the medical procedure.

With this approach, however, there is the risk of a blood vessel not being adequately visible and palpable through the recess and through the sealing layer with the gel medium because only a relatively small recess is provided in an otherwise nontransparent backing layer. Likewise, there is the risk that the puncture. site and the area around the puncture site may be inadequately disinfected prior to the puncture. Since only the thin elastic sealing layer with the gel medium is effective at the puncture site itself, there is increased risk that blood may escape after the needle is extracted and therefore additional measures are required for hemostasis.

The object of the present invention is therefore to provide an improved self-closing antiseptic plaster.

The antiseptic effect of the plaster should consist of keeping the puncture site and the area in its immediate vicinity antiseptic before, during and after the puncture and should do so in a reliable manner and as easily as possible. In addition, the escape of blood after extraction of the needle from the puncture wound should be prevented as best as can be in order to protect the medical and nursing personnel from possible infections and to facilitate the subsequent hemostasis that might be necessary.

This object is achieved through the features of Patent Claim 1.

The means of achieving this object consists of applying a self-closing antiseptic plaster to the previously cleaned and disinfected body site and thereby sealing the site that is to be punctured in its antiseptic state. The self-closing antiseptic plaster has a continuous backing layer without recesses. The entire backing layer of the plaster is provided with a skin adhesive layer on the side coming in contact with the skin. A sealing layer having self-sealing properties is applied to the backing layer by means of an adhesive layer. Furthermore, the backing layer, the sealing layer, the adhesive layer and the skin adhesive layer are preferably transparent or approximately transparent in the entire area of the self-closing antiseptic plaster or at least in a superimposed partial area thereof. The plaster may thus also be left on the puncture site after the procedure has been completed and thus ensures a persistent antiseptic condition.

By introducing a backing layer and a sealing layer with self-sealing properties thereon by means of an adhesive layer, this achieves the result that a multitude of suitable materials having self-sealing properties can be used for the sealing layer without being hindered from using same at the same time because of lack of suitable and fitting skin adhesive layers, e.g., those enriched with antiallergic, antiseptic or analgesic active ingredients. The backing layer thus serves to provide a certain "uncoupling" of the functions and also serves to stabilize the mechanical properties of the sealing layer, e.g., the extensibility which is necessary and desired with certain materials having favorable self-sealing properties such as silicone.

The backing layer and the sealing layer are also advantageously designed to be water-vapor-permeable to facilitate as much as possible the transport of moisture away from the skin to the ambient environment. The backing layer may also have liquid absorbing properties.

Due to the extent of the of the backing layer and the sealing layer applied thereto over the entire area of the self-closing antiseptic plaster, such that they are substantially co-extensive with each other along at least one cross-sectional dimension as shown in FIGS. 1 and 2, as well as the transparency of all layers provided, the achieves the result that placement and use of the self-closing antiseptic plaster are greatly facilitated. The visibility of the site to be punctured and especially also the palpability of blood vessels are significantly improved in comparison with an approach having recesses. The greater palpability of blood vessels is of course also facilitated by the fact that both the backing material and the sealing layer are made of thin soft materials. In addition, however, this also achieves the result that the puncture site itself is sealed again as tightly and elastically as it would be with a type of additional "synthetic skin" and is self-sealing again after extraction of the needle or cannula out of the puncture site, so that in the normal case no blood can escape from the puncture channel.

Silicone suitable for medicinal purposes is preferably used as the material for the sealing layer. It not only has excellent properties with regard to tolerability with the human or animal body but also in particular has excellent properties with regard to extensibility respectively the elastic restoring force. This latter property also has the effect that a puncture channel created by as needle or cannula is virtually sealed again automatically and immediately after retraction of the needle so that no blood escapes. Another effect is that although the material is cut on the first millimeters in the puncture, it is then pushed apart, i.e. displaced, so this reliably prevents punching out or separating material particles that might enter the patient's body.

On the other hand however silicone is a material that cannot be glued reliably to all other materials with no problem. One problem that has not yet been solved satisfactorily in particular is that of achieving reliable, direct and permanent application of an adhesive which additionally also has the desired properties with regard to being tolerated by the skin. Therefore, the backing layer that is used has proven to be doubly beneficial of course also with regard to the desired stabilizing effect because of the extremely high extensibility of silicone. The inventive application of an adhesive between the sealing layer and the backing layer does not require it to have any properties specific to a skin adhesive but instead may be approved only for medicinal applications.

It is also possible to provide for an adhesive-free recess to be provided in the adhesive layer between the sealing layer and the backing layer in an area provided for needle punctures. This achieves the result that even when punctured with a needle or cannula, it is certain that no traces of material particles of the adhesive can enter the patient's body.

Furthermore, it is also possible for the adhesive layer, which in the simplest case comprises only one adhesive (also termed as an industrial adhesive, i.e., an adhesive without specific properties pertaining to a skin adhesive) to have a backing film which is provided with adhesive on both sides. Such a structure of the adhesive layer may be selected to simplify production in the sense that it may be used as a "supplier part" for the production of the self-closing antiseptic plaster.

Since the backing layer itself also has a certain extensibility, although minor, the extraordinarily great extensibility of silicone is limited and stabilized by the backing layer in its areal extensibility. This exerts a certain pressure acting on the puncture wound for the purpose of hemostasis.

To improve the continuous contact of silicone with the adhesive used, a surface treatment of the silicone may also be provided, such as a plasma treatment, a corona treatment, a wet chemical treatment or some other treatment.

Of course other materials with self-sealing properties and/or a high elastic restoring force may also be used for the sealing layer, e.g., rubber, natural or synthetic, latex, hydrogel, polymer plastics. Likewise, combinations of these materials, even with silicone, may also be used.

The total thickness of an inventive self-closing antiseptic plaster preferably varies approximately in the range of 1.0 to 5 mm.

For the purpose of protecting the skin adhesive, the self-closing antiseptic plaster is preferably provided with removable protective films on the skin adhesive side.

The inventive self-closing antiseptic plaster may of course also be produced in suitable sizes and geometric shapes, depending on the intended medical application. However, it is preferably designed to be flat, so it is especially easy to handle in production and also in the cut-to-size forms. However, non-flat designs, e.g., slightly lenticular designs, may also be provided.

The inventive self-closing antiseptic plaster is described in greater detail below on the basis of an exemplary embodiment with drawings.

Figure 1:
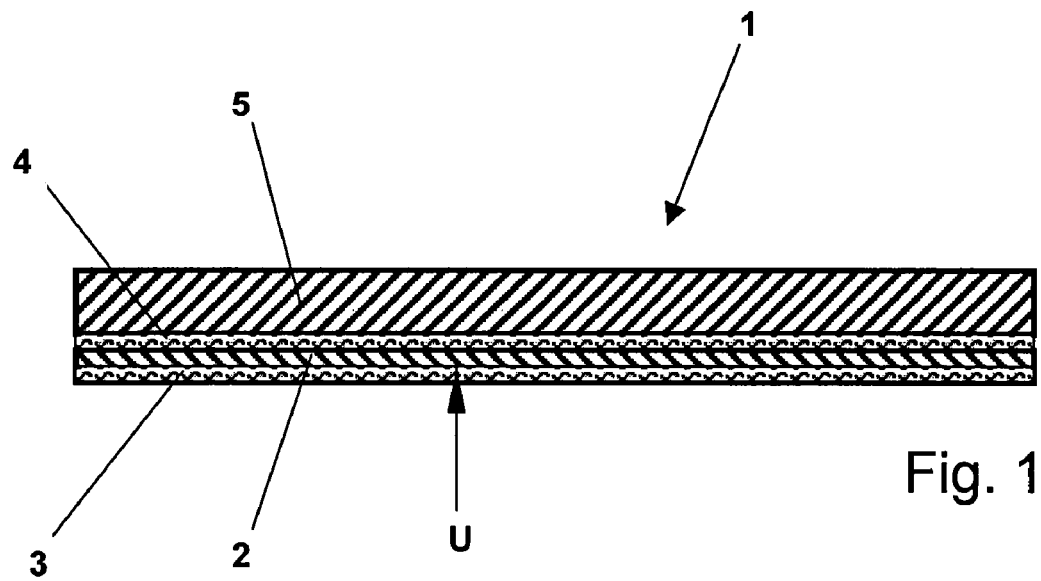
FIG. 1 shows a cross section through a self-closing antiseptic plaster.

FIG. 1 shows a cross section not drawn to scale through a self-closing antiseptic plaster 1. A backing layer, usually thin, is provided with adhesive layers on both sides. A (medicinal) skin adhesive layer 3 is provided on the underside U of the backing layer 2, whereby this side of the self-closing antiseptic plaster 1 is intended for adhesive application to human skin. On the other side of the backing layer 2 there is an (industrial) adhesive layer 4. The adhesive layer 4 is between the backing layer 2 and a sealing layer 5 and does not have any properties specific to a skin adhesive. Since materials such as silicone are used for the sealing layer 5, the only adhesives known for use with these materials have little or no compatibility with skin, the adhesive layer 4 with this design of the self-closing antiseptic plaster 1 need not have any properties that are specific for a skin adhesive, i.e., being especially gentle to skin, because it does not come in contact with the skin. The adhesive for the adhesive layer 4 need only be suitable for medicinal purposes.

All the layers used, i.e., the backing layer 2, the sealing layer 5, the adhesive 4 and the skin adhesive layer 3 are preferably transparent or approximately transparent in the entire area of the self-closing antiseptic plaster 1 or at least in a sufficiently large superimposed partial area thereof. Furthermore, thin and soft materials are provided for the backing layer 2 and the sealing layer 5 so that the puncture site is visible and readily palpable through the self-closing antiseptic plaster.

The backing layer 2 is preferably made of a material that is less extensible than the sealing layer 5. Thus the higher extensibility of the sealing layer 5 is limited and stabilized in its areal extent. If a layer structure including a backing film and an (industrial) adhesive applied to both sides of the backing film is used for the adhesive layer 4, then one may of course expect that this backing film, like the backing layer 2 and naturally also depending on the choice of materials, will contribute toward the limitation of extensibility and the stabilization of the sealing layer 5.

The backing layer 2 is usually thin, preferably also water-vapor-permeable outside of a puncture area and is having a thickness in the range of 0.01 to approximately 1 mm. To be able to achieve a water vapor permeability or absorption capacity, materials such as a nonwoven or paper may be used.

In another embodiment, the backing layer 2 is made of polyurethane, for example, is very thin (film-like) and has a thickness in the range of 0.01 to 0.05 mm. However, other materials such as polyethylene may also be used.

The sealing layer 5 is preferably made of silicone and has a thickness in the range of 1 to 5 mm. However, other materials such as rubber, natural or synthetic, latex, hydrogel, polymer plastics or a combination of these materials having self-sealing properties may be used.

It is also assumed that those skilled in the art will be sufficiently familiar with the adhesives that may be used, i.e., those having suitable properties for the adhesive layer 4 and the skin adhesive layer 3. In the case of the skin adhesive layer in particular, it may be assumed that as a rule an adhesive having one or more properties from the following group of properties must be selected by adding the corresponding active ingredients:

antiseptic properties,
antiallergic properties,
analgesic properties, etc.

If silicone is used as the sealing layer 5, it may be necessary to prepare the contact surface of the silicone with an adhesive layer 4 in a suitable manner. To improve the permanent contact of silicone with the adhesive being used, a surface treatment such as a plasma treatment, a corona treatment, a wet chemical treatment or some other treatment may be provided.

Figure 2:
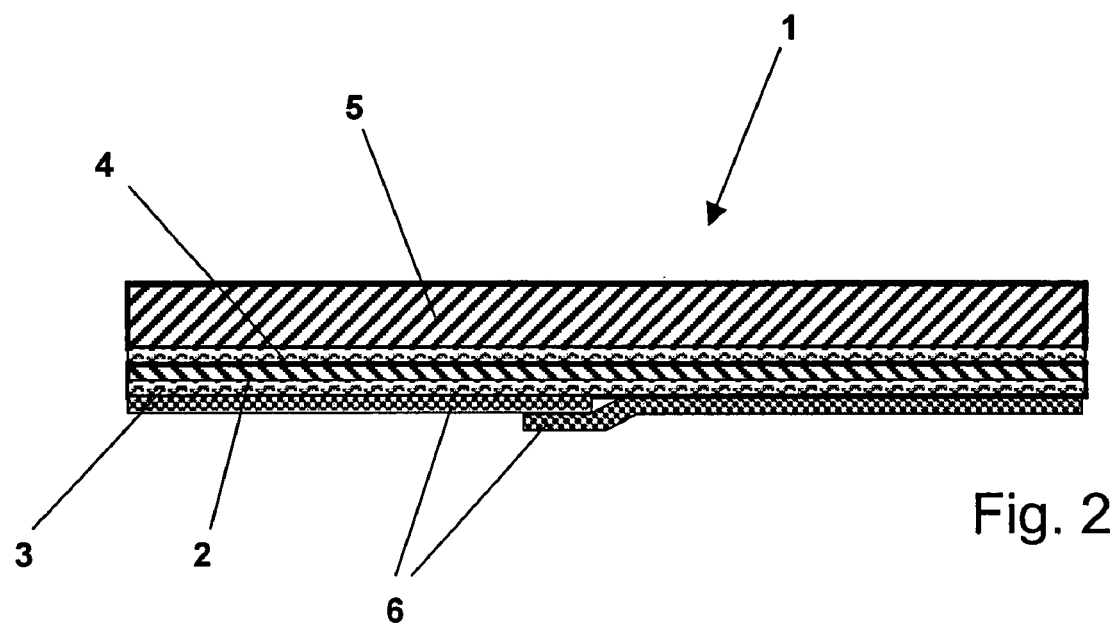
FIG. 2 shows a cross section through a self-closing antiseptic plaster according to FIG. 1 with removable protective films.

Finally, FIG. 2 shows a cross section through a self-closing antiseptic plaster according to FIG. 1 with removable protective films 6.

Use of the self-closing antiseptic plaster:

The puncture site is localized.

The body location to be punctured is cleaned and disinfected in the traditional way, At the self-closing antiseptic plaster 1, the protective films 6 are pulled away and the plaster 1 is adhesively applied to the respective body site with the underside U of the backing layer 2 to which the skin adhesive layer 3 is applied. This preserves the antiseptic state prior to the puncture.

For the puncture of a blood vessel, of tissue, of skin, of organs (biopsy) or a bone marrow, the site is localized again visually and/or by palpation through the transparent surface of the self-closing antiseptic plaster.

The puncturing is performed by puncturing the self-closing antiseptic plaster, i.e. all the layers thereof with a needle or cannula or the like. The intended amount of liquid and/or tissue is removed from the patient being treated through the needle or cannula or only fluid is supplied to the patient. Since it is always assumed that the procedure is being performed by professional medical personnel, it is also assumed that the syringe or cannula being used will already be sterile. The antiseptic state is thus preserved even during the puncturing. Because of the elastic restoring force of the sealing layer 5, it also protects the site to be punctured from ambient influences during the procedure because the material is always in tight contact with the needle or cannula. Furthermore, the personnel are protected from possible infections.

After the procedure is completed, the needle or cannula is extracted. Again, the elastic restoring force of the sealing layer 5 acts in such a way that the puncture channel is sealed immediately again due to the restoring force of the sealing layer. Thus the punctured site is reliably protected again even after the procedure. No microorganisms, microscopic and/or macroscopic dirt particles and/or viruses and/or bacteria can enter the puncture channel and thus the human or animal body.

Due to the design of the self-closing antiseptic plaster described here, leakage of blood from the puncture wound is precluded in the normal case. In puncturing blood vessels, under some circumstances, as long as the patient is physically or mentally capable of doing so, he/she may additionally compress the puncture site by pressing on the self-closing antiseptic plaster until the puncture site has sealed itself through coagulation of blood. The self-closing antiseptic plaster may at any rate remain on the respective body site as long as is necessary or as long as desired.

LIST OF REFERENCE NOTATION 1 plaster
2 backing layer
3 (medicinal) skin adhesive layer
4 (industrial) adhesive layer
5 sealing layer
6 protective film
U underside of the backing layer

The invention claimed is:

1. A self-closing antiseptic plaster for puncturing blood vessels, muscle tissue, tissue, skin, organs and bone marrow, puncturable by cannulas or needles and transparent in a partial area, comprising:

a backing layer having no recesses and at least a first side and a second side, a transparent and puncturable sealing layer made of a material having an elastic restoring force attached to the backing layer, a first adhesive layer coupled to said first side of said backing layer, a second adhesive layer comprising a skin adhesive layer applied to an entire second side which is an underside of said backing layer, and wherein said backing layer and said sealing layer, are transparent or approximately transparent and said backing layer and said sealing layer are substantially co-extensive with each other along at least one cross-sectional dimension of the antiseptic plaster.

2. The self-closing antiseptic plaster according to claim 1, wherein
the backing layer and the sealing layer are made of thin and soft materials so that the site to be punctured can be palpated through the self-closing antiseptic plaster.

3. The self-closing antiseptic plaster according to claim 1, wherein
the backing layer and/or the sealing layer is/are water-vapor-permeable outside of a puncture area.

4. The self-closing antiseptic plaster according to claim 1, wherein
the backing layer has stabilizing properties and is less extensible than the sealing layer.

5. The self-closing antiseptic plaster according to claim 4, wherein
said backing layer is made of polyurethane and has a thickness in the range of 0.01-0.05 mm.

6. The self-closing antiseptic plaster according to claim 1, wherein
the backing layer is liquid absorbent.

7. The self-closing antiseptic plaster according to claim 1, wherein
said first adhesive layer need not have any properties specific to a skin adhesive.

8. The self-closing antiseptic plaster according to claim 1, wherein
said first adhesive layer has an adhesive-free recess in an area provided for needle punctures.

9. The self-closing antiseptic plaster according to claim 1, wherein
the backing layer is provided with said first adhesive layer on the one side and said skin adhesive layer on the other side.

10. The self-closing antiseptic plaster according to claim 1, wherein
said skin adhesive layer has one or more of the properties from the following group of properties due to the addition of appropriate active ingredients:

antiseptic properties, antiallergic properties, analgesic properties.

11. The self-closing antiseptic plaster according to claim 1, wherein said sealing layer is at least partially made of rubber, natural or synthetic, latex, silicone, hydrogel, polymer plastics or a combination of these materials and has self-sealing properties.

12. The self-closing antiseptic plaster according to claim 1, wherein said sealing layer is made of silicone pretreated on said second adhesive layer side by a plasma treatment, a corona treatment or a wet chemical treatment.

13. The self-closing antiseptic plaster according to claim 12, wherein the antiseptic plaster has a total thickness in the range of 1 to 5 mm.

14. A self-closing antiseptic plaster for puncturing blood vessels, muscle tissue, tissue, skin, organs and bone marrow, puncturable by cannulas or needles and transparent in partial area, comprising:

a backing layer having no recesses and at least a first side and a second side, a transparent and puncturable sealing layer made of a material having an elastic restoring force attached to the backing layer, a first adhesive layer coupled to said first side of said backing layer and which is provided between the backing layer and the sealing layer, and a second adhesive layer applied to the entire second side which is an underside of the backing layer, the backing layer and the sealing layer are transparent or approximately transparent and both said backing layer and said sealing layer are substantially co-extensive with each other along at least one cross-sectional dimension of the antiseptic plaster.

* * * * *